United States Patent
Choi et al.

(10) Patent No.: US 9,931,307 B2
(45) Date of Patent: Apr. 3, 2018

(54) TRANSDERMAL DELIVERY SYSTEM COMPRISING DONEPEZIL OR ITS SALT

(71) Applicant: DAEWOONG PHARMACEUTICAL CO., LTD., Seongnam-si, Gyeonggi-do (KR)

(72) Inventors: Yo-Han Choi, Yongin-si (KR); Hee-Chul Chang, Seoul (KR)

(73) Assignee: DAEWOONG PHARMACEUTICAL CO., LTD., Seongnam-si, Gyeonggi-do (KR)

( * ) Notice: Subject to any disclaimer, the term of this patent is extended or adjusted under 35 U.S.C. 154(b) by 0 days.

(21) Appl. No.: 14/779,649

(22) PCT Filed: Jan. 12, 2015

(86) PCT No.: PCT/KR2015/000277
§ 371 (c)(1),
(2) Date: Sep. 24, 2015

(87) PCT Pub. No.: WO2015/111862
PCT Pub. Date: Jul. 30, 2015

(65) Prior Publication Data
US 2016/0051486 A1    Feb. 25, 2016

(30) Foreign Application Priority Data
Jan. 22, 2014  (KR) .......................... 10-2014-0007556

(51) Int. Cl.
*A61K 9/70*       (2006.01)
*A61K 31/445*   (2006.01)

(52) U.S. Cl.
CPC .......... *A61K 9/7053* (2013.01); *A61K 31/445* (2013.01)

(58) Field of Classification Search
None
See application file for complete search history.

(56) References Cited

U.S. PATENT DOCUMENTS

| | | | |
|---|---|---|---|
| 6,815,454 B2 | 11/2004 | Murahashi et al. | |
| 2004/0258741 A1 | 12/2004 | Terahara et al. | |
| 2006/0257461 A1* | 11/2006 | Jansen | A61F 13/0203 424/448 |
| 2008/0044461 A1 | 2/2008 | Valia et al. | |
| 2009/0175929 A1 | 7/2009 | Terahara et al. | |
| 2010/0080842 A1 | 4/2010 | Wen et al. | |
| 2011/0243998 A1* | 10/2011 | Sakamoto | A61K 9/7053 424/400 |
| 2012/0029446 A1 | 2/2012 | Amano et al. | |
| 2012/0207816 A1 | 8/2012 | Kawakami et al. | |
| 2013/0165875 A1* | 6/2013 | Choi | A61K 9/7053 604/307 |

FOREIGN PATENT DOCUMENTS

| | | |
|---|---|---|
| KR | 2001-0045185 A | 6/2001 |
| KR | 10-2004-0018672 A | 3/2004 |
| KR | 10-2009-0101667 A | 9/2009 |
| KR | 10-2011-0030349 A | 3/2011 |
| KR | 10-2011-0109995 A | 10/2011 |
| WO | 2005/123046 A1 | 12/2005 |

OTHER PUBLICATIONS

N-Methyl-2-pyrrolidone, accessed from the Internet at <https://en.wiki-pedia.org/wiki/N-Methyl-2-pyrrolidone> on Apr. 19, 2017.*

* cited by examiner

*Primary Examiner* — David J Blanchard
*Assistant Examiner* — Daniel F Coughlin
(74) *Attorney, Agent, or Firm* — Vorys, Sater, Seymour & Pease LLP; Mih Suhn Koh

(57) ABSTRACT

Provided is a transdermal delivery system consisting of a backing layer, a drug-containing matrix layer, and a release layer, wherein the drug-containing matrix layer includes (a) donepezil or a pharmaceutically acceptable salt thereof as an active ingredient, (b) a mixture of high molecular weight polyisobutylene having a weight-average molecular weight ranging from 400,000 to 3,000,000 and low molecular weight polyisobutylene having a weight-average molecular weight ranging from 25,000 to 300,000 as an adhesive, and (c) a permeation enhancer in not more than 3% by weight based on the total weight of the drug-containing matrix layer.

1 Claim, 9 Drawing Sheets

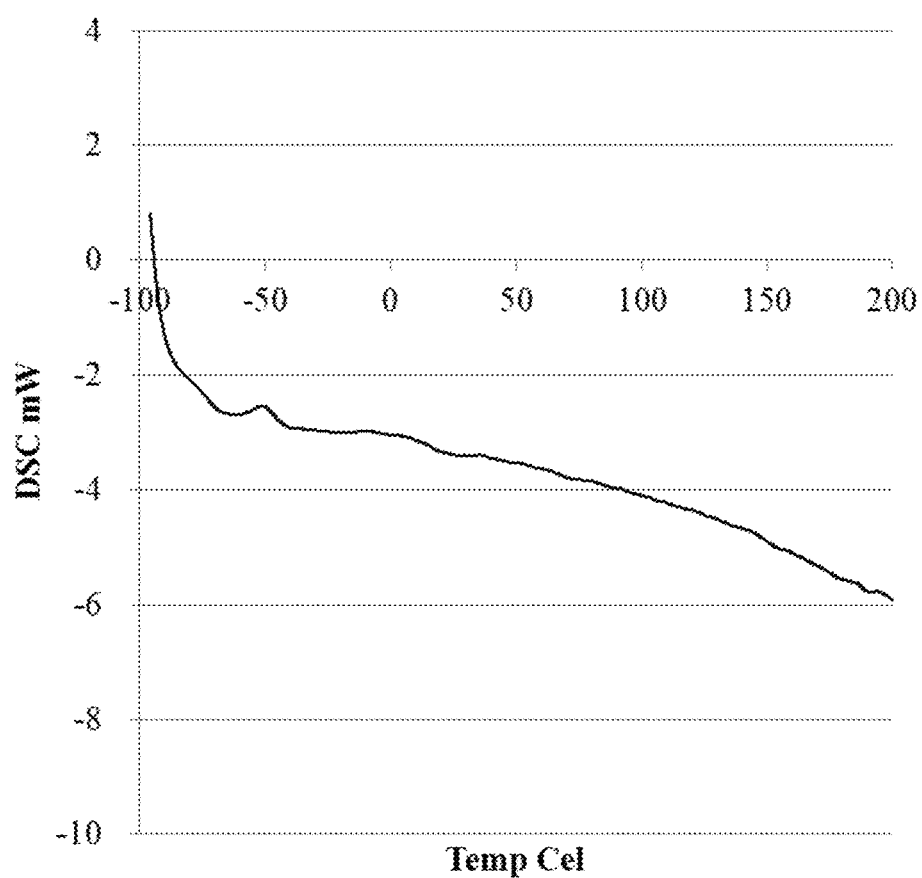

TRANSDERMAL DELIVERY SYSTEM COMPRISING DONEPEZIL OR ITS SALT

TECHNICAL FIELD

The present invention relates to a transdermal delivery system comprising donepezil or its salt. More specifically, the present invention relates to a transdermal delivery system comprising a drug-containing matrix layer having a single-layer structure, in which the drug-containing matrix layer comprises a mixture of high molecular weight polyisobutylene and low molecular weight polyisobutylene as an adhesive and a permeation enhancer in not more than 3% by weight.

BACKGROUND ART

Patients suffering from Alzheimer's disease show significantly decreased levels of cholinergic neurons and acetylcholine secretion in most of the cerebral cortex. Therefore, it has been known that cognitive impairment in the patients can be ameliorated by increasing the cerebral acetylcholine level. Acetylcholinesterase inhibitors inhibit the acetylcholinesterase (AChE) to increase the cerebral acetylcholine level, thereby being used for the management of Alzheimer's disease symptoms. Currently developed acetylcholinesterase inhibitors include tacrine (1993), donepezil (1996), rivastigmine (1999) and galantamine (2001), which were approved by the U.S. Food and Drug Administration (FDA) for treating Alzheimer's disease. For example, Aricept™ (Eisai), donepezil-containing tablet, is an oral formulation which is administered once daily at bedtime.

Meanwhile, it has been known that oral administration of the donepezil-containing tablet causes gastrointestinal side effects such as diarrhea, vomiting, loss of appetite, and muscle cramps. And also, the patients suffering from Alzheimer's disease should repeatedly take the drug once every day (at bedtime), which results in lowering patients' compliance, thereby making it difficult to maintain the pharmacological effect thereof continuously. Therefore, a donepezil-containing transdermal delivery system is expected to avoid the gastrointestinal side effects according to oral administration and improve patients' compliance. Especially, a transdermal delivery system is expected to continuously maintain the desired pharmacological effect, through releasing the drug substance in continuous manner for a long period of time.

There have been disclosed various transdermal delivery systems comprising donepezil or its salt. For example, transdermal delivery systems comprising donepezil or its salt have been disclosed in various prior arts including U.S. Pat. No. 6,815,454, US Patent Publication No. 2009/0175929, US Patent Publication No. 2010/0080842, US Patent Publication No. 2012/0207816, WO 2003/032960, Korean Patent Publication No. 10-2009-0101667, Korean Patent Publication No. 10-2011-0030349, Korean Patent Publication No. 10-2011-0109995, etc.

However, most of the transdermal delivery systems disclosed in prior arts involve the use of various permeation enhancers in a large amount in order to overcome the low skin permeation rate of drug substance, which causes adverse events such as rashes or skin irritation.

And also, it is difficult to maintain skin permeation rate in a desired level for a long period of time (e.g., for 7 days or more), which is necessary for improving patients' compliance. For example, in case of the transdermal delivery system disclosed in WO2003/032960, the skin permeation rate reaches maximum level of 2~2.5 $\mu g/cm^2/hr$ and then decreased rapidly. At 48 hours after applying the transdermal delivery system, the skin permeation rate thereof is decreased to about 1 $\mu g/cm^2/hr$, which makes it difficult to maintain the therapeutic effect continuously. And also, there have been disclosed transdermal delivery systems wherein a release-controlling layer is inserted between two or more drug-containing layers (e.g., Korean Patent Publication No. 10-2011-0030349, EP 2,399,607, etc.). However, the transdermal delivery systems having a multi-layer structure have problems such as complicated manufacturing processes in industrial mass production; and high production cost.

In addition, crystallization of drug substance in a transdermal delivery system causes various problems, such as decrease in adhesive force, variation in skin permeation rate, storage problems, etc., which make it difficult to incorporate drug substance in a high concentration into a transdermal delivery system. US Patent Publication Nos. 2010/0080842 and 2009/0175929 have disclosed a transdermal delivery systems obtained by using an acrylic pressure-sensitive adhesive having carboxylic acid functionalities or hydroxyl functionalities, as well as using a specific permeation enhancer or a specific crystal form of donepezil (type-B crystal polymorphism) or a specific crystallization-inhibiting agent (i.e., a (meth)acrylate copolymer having a carboxylic group). However, if an acrylic pressure-sensitive adhesive is used as a matrix of the transdermal delivery system, the drug diffusion is slowed in the pressure-sensitive adhesive layer due to the interaction between donepezil and the acrylic polymer in the layer, which also reduces movement of the drug from the pressure-sensitive adhesive layer to the skin. In order to solve this problem, Korean Patent Publication No. 10-2009-0101667 has disclosed a transdermal delivery system obtained by using an EVA (ethylene vinyl acetate) adhesive and a rosin ester resin as a crystallization-inhibiting agent.

Therefore, there is a need to develop a transdermal delivery system which can solve said problems, such as adverse events (e.g., rashes or skin irritation); difficulties in maintaining the skin permeation rate for a long period of time (e.g. for 7 days or more); complicated manufacturing processes and high production cost associated with forming a release-controlling layer additionally; and problems originated from crystallization in the matrix (e.g., decrease in adhesive force, variation in skin permeation rate, and difficulty in incorporating drug substance in a high concentration, etc.). Especially, in designing a transdermal delivery system used for a long period of time such as 7 days or more, selection of the optimum adhesive is very critical for both minimizing potential variation in skin permeation rate and avoiding any potential crystallization, which are originated from interaction between drug substance and an adhesive. And also, there is a need to develop a transdermal delivery system comprising a drug-containing matrix layer having a single-layer structure that is easily applicable to industrial mass production, the transdermal delivery system of which can release a drug continuously, thereby achieving the therapeutic effects for a long period of time (for 7 days or more) even when applied only once; requires using a permeation enhancer in a small amount; and has excellent physicochemical stability. In addition, other problems, such as air bubble formation in the formulation and deformation after applying the formulation to the skin, should be also solved to achieve consistency and/or continuity in skin permeation rate of drug substance.

DISCLOSURE OF INVENTION

Technical Problem

The present invention provides a donepezil or its salt-containing transdermal delivery system comprising a drug-containing matrix layer having a single-layer structure, which exhibits high skin permeation rate in continuous manner for a long period of time (at least, for 7 days or more) even containing a permeation enhancer in a small amount of not more than 3% by weight in the drug-containing matrix layer; and shows low skin irritation and excellent physicochemical stability.

Specifically, it is an object of the present invention to provide a donepezil or its salt-containing transdermal delivery system which exhibits high skin permeation rate continuously for 7 days or more; and shows low skin irritation and excellent stability.

Solution to Problem

In accordance with an aspect of the present invention, there is provided a transdermal delivery system consisting of a backing layer, a drug-containing matrix layer, and a release layer, wherein the drug-containing matrix layer comprises (a) donepezil or a pharmaceutically acceptable salt thereof as an active ingredient, (b) a mixture of high molecular weight polyisobutylene having a weight-average molecular weight ranging from 400,000 to 3,000,000 and low molecular weight polyisobutylene having a weight-average molecular weight ranging from 25,000 to 300,000 as an adhesive, and (c) a permeation enhancer in not more than 3% by weight based on the total weight of the drug-containing matrix layer.

In the transdermal delivery system of the present invention, donepezil or a pharmaceutically acceptable salt thereof may be present in an amount of 5 to 10% by weight based on the total weight of the drug-containing matrix layer.

The high molecular weight polyisobutylene may have a weight-average molecular weight ranging from 800,000 to 1,500,000, and the low molecular weight polyisobutylene may have a weight-average molecular weight ranging from 25,000 to 200,000. In an embodiment, the adhesive may be a mixture of high molecular weight polyisobutylene having a weight-average molecular weight of 1,000,000 and low molecular weight polyisobutylene having a weight-average molecular weight of 75,000. A weight ratio of the high molecular weight polyisobutylene and the low molecular weight polyisobutylene may be 1:0.3 to 1:2. And also, the adhesive may be present in an amount of 40 to 50% by weight based on the total weight of the drug-containing matrix layer.

The permeation enhancer may be present in an amount of 0.5 to 2.5% by weight based on the total weight of the drug-containing matrix layer. In an embodiment, the permeation enhancer is lauryl pyrrolidone.

In the transdermal delivery system of the present invention, the drug-containing matrix layer may further comprise one or more excipients selected from the group consisting of a stabilizer, an oil, and a thickening agent. In an embodiment, the stabilizer is butylated hydroxytoluene.

Advantageous Effects of Invention

The transdermal delivery system according to the present invention comprises a drug-containing matrix layer having a single-layer structure, in which the drug-containing matrix layer comprises a mixture of high molecular weight polyisobutylene and low molecular weight polyisobutylene as an adhesive; and a permeation enhancer in not more than 3% by weight. Since the transdermal delivery system of the present invention has a single-layer structure, it can be easily applied to industrial mass production and produced cost effectively compared to transdermal delivery systems having a multiple-layer structure. Especially, the transdermal delivery system of the present invention includes a permeation enhancer in very small amount, thereby being able to minimize skin irritation. The transdermal delivery system of the present invention also can maintain high skin permeation rate continuously for a long period of time (at least, for 7 days or more) by using the combination of high molecular weight polyisobutylene and low molecular weight polyisobutylene. And also, the transdermal delivery system according to the present invention can prevent from crystallization of donepezil even when stored for a long period of time, while maintaining the skin permeation rate. Therefore, the transdermal delivery system according to the present invention can significantly improve patients' compliance in Alzheimer's disease.

BRIEF DESCRIPTION OF DRAWINGS

FIGS. 7a and 7b show the results of differential scanning calorimetry analyses on the transdermal delivery system prepared according to the present invention using a Differential Scanning calorimeter, after 1 month of storage at room temperature condition (25° C., relative humidity of 60%) and at accelerated storage condition (40° C., relative humidity of 75%), respectively.

BEST MODE FOR CARRYING OUT THE INVENTION

Figure 1:
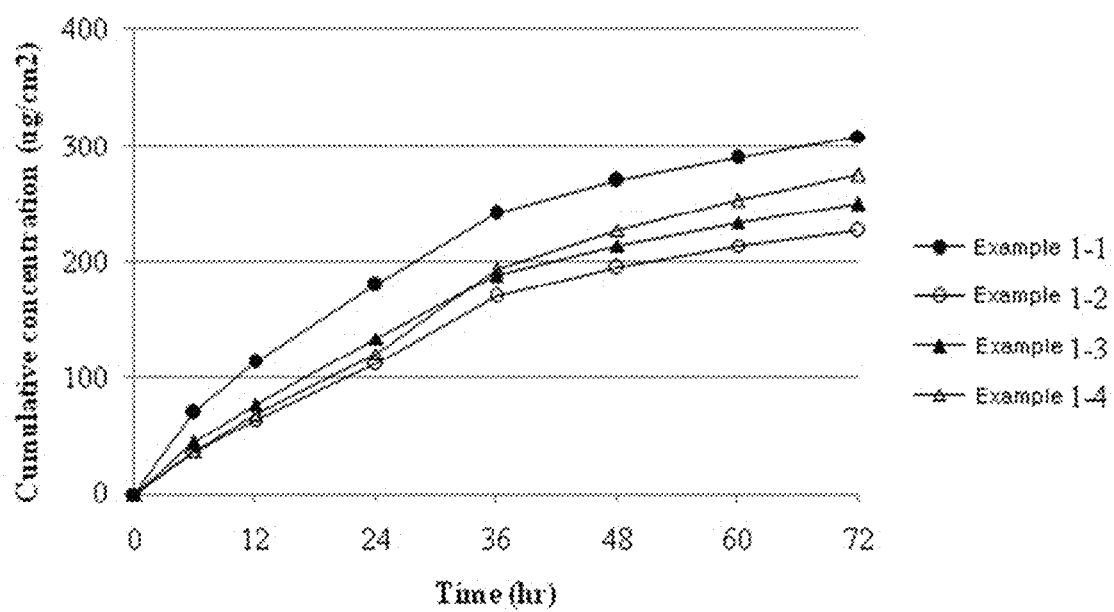
FIG. 1 shows the results obtained by measuring skin permeation rate (cumulative concentration) after applying the transdermal delivery systems according to the present invention to the hairless mouse skin.

The present invention provides a transdermal delivery system consisting of a backing layer, a drug-containing matrix layer, and a release layer, wherein the drug-containing matrix layer comprises (a) donepezil or a pharmaceutically acceptable salt thereof as an active ingredient, (b) a mixture of high molecular weight polyisobutylene having a weight-average molecular weight ranging from 400,000 to 3,000,000 and low molecular weight polyisobutylene having a weight-average molecular weight ranging from 25,000 to 300,000 as an adhesive, and (c) a permeation enhancer in not more than 3% by weight based on the total weight of the drug-containing matrix layer.

In the transdermal delivery system according to the present invention, the donepezil or a pharmaceutically acceptable salt thereof may be used in an amount sufficient to obtain therapeutically effective blood concentration. Surprisingly, It has been found that when donepezil or a pharmaceutically acceptable salt thereof is used in a specific amount, specifically in an amount of 5 to 10% by weight, preferably in about 7.6% by weight based on the total weight of the drug-containing matrix layer, the resulting transdermal delivery system can maintain high skin permeation rate continuously for a long period of time (for 7 days or more), while avoiding any potential decrease in skin permeation rate that may be originated from crystallization of drug substance.

In the transdermal delivery system according to the present invention, the drug-containing matrix layer has a single-layer structure, which is achieved by using two kinds of polyisobutylene as an adhesive, i.e., a mixture of high molecular weight polyisobutylene having a weight-average molecular weight ranging from 400,000 to 3,000,000 and low molecular weight polyisobutylene having a weight-average molecular weight ranging from 25,000 to 300,000. The use of specific combination of the adhesives makes it possible to prepare a drug-containing matrix layer having donepezil or its salt in the amount required to maintain high skin permeation rate continuously for a long period of time (for 7 days or more) while avoiding any potential decrease in skin permeation rate that may be originated from crystallization of drug substance (i.e., in an amount of 5 to 10% by weight, preferably in about 7.6% by weight based on the total weight of the drug-containing matrix layer). And also, the use of specific combination of the adhesives makes it possible to effectively solve the problems such as air bubble formation in the formulation and deformation (i.e., being shoved) after applying the formulation to the skin.

When only high molecular weight polyisobutylene is used as an adhesive, the adhesive force gets to be too strong, which makes it not suitable for applying to industrial mass-production and causes problems in removing a release liner from the resulting transdermal delivery system. The mixture of high molecular weight polyisobutylene and low molecular weight polyisobutylene forms a matrix in the drug-containing matrix layer. That is, donepezil or a pharmaceutically acceptable salt thereof is homogeneously dispersed in the mixture of high molecular weight polyisobutylene and low molecular weight polyisobutylene, thereby forming the drug-containing matrix layer. Therefore, the transdermal delivery system of the present invention can be prepared by simplified processes compared to the transdermal delivery systems having a multiple-layer structure, which leads to easy scale-up and reduced production cost. And also, the transdermal delivery system of the present invention can maintain skin permeation rate continuously for a long period of time (for 7 days or more), while being stably attached to human skin.

The high molecular weight polyisobutylene may have a weight-average molecular weight ranging from 400,000 to 3,000,000, preferably from 800,000 to 1,500,000, more preferably about 1,000,000. If necessary, commercially available high molecular weight polyisobutylene (e.g., Oppanol™ B 100, BASF, Germany) may be used. The low molecular weight polyisobutylene may have a weight-average molecular weight ranging from 25,000 to 300,000, preferably from 25,000 to 200,000, more preferably about 75,000. If necessary, commercially available low molecular weight polyisobutylene (e.g., Oppanol™ B 10, Oppanol™ B S15F, Oppanol™ B 30 etc., BASF, Germany) may be used. In an embodiment, the adhesive may be a mixture of high molecular weight polyisobutylene having a weight-average molecular weight of about 1,000,000 and low molecular weight polyisobutylene having a weight-average molecular weight of about 75,000. A weight ratio of the high molecular weight polyisobutylene and the low molecular weight polyisobutylene may be in an amount of 1:0.3 to 1:2, preferably about 1:1, but is not limited thereto. The adhesive may be present in an amount of 40 to 50% by weight based on the total weight of the drug-containing matrix layer.

The permeation enhancer is present in not more than 3% by weight, preferably in an amount of 0.5 to 2.5% by weight, based on the total weight of the drug-containing matrix layer. The transdermal delivery system of the present invention contains the permeation enhancer in a small amount, thereby minimizing skin irritation. Especially, the transdermal delivery system of present invention can maintain high skin permeation rate continuously for a long period of time (for 7 days or more) even containing the permeation enhancer in a small amount. Examples of the permeation enhancer include isopropyl myristate, lauryl pyrrolidone, lauryl alcohol etc., and preferably lauryl pyrrolidone.

The drug-containing matrix layer may further comprise one or more excipients selected from the group consisting of a stabilizer, an oil, and a thickening agent conventionally used in the field of a transdermal delivery system. It has been newly found by the present invention that, when butylated hydroxytoluene is used as a stabilizer, the stability of the formulation can be effectively maintained. Therefore, butylated hydroxytoluene may be preferably used as a stabilizer. The stabilizer may be used in a suitable amount. For example, the stabilizer may be used in an amount of 0.1 to 2% by weight, preferably about 0.3% by weight, based on the total weight of the drug-containing matrix layer. Examples of the oil include mineral oil (e.g., Samchun™ M7319 etc.). The oil functions as a plasticizer in forming a drug-containing matrix layer. The oil may be used in a suitable amount. For example, the oil may be used in an amount of 15 to 20% by weight, preferably about 18% by weight, based on the total weight of the drug-containing matrix layer. And also, Examples of the thickening agent include conventional viscosity-increasing agents, such as hydrocarbon resin (e.g., Kristalex™ F85, Piccotac™ 1020, 1095, Escorez™ 5000, Koresin™ etc.). The amount of thickening agent depends on the type of thickening agents, but the thickening agent may be used in an amount of 20 to 40% by weight, preferably about 25 to 28% by weight, based on the total weight of the drug-containing matrix layer.

In an embodiment of the present invention, there is provided a transdermal delivery system consisting of a backing layer, a drug-containing matrix layer, and a release layer, wherein the drug-containing matrix layer consists of 7.6% by weight of donepezil or a pharmaceutically acceptable salt thereof; 22.7% by weight of polyisobutylene having a weight-average molecular weight of 1,000,000; 22.7% by weight of polyisobutylene having a weight-average molecular weight of 75,000; 1.5% by weight of lauryl pyrrolidone; 0.3% by weight of butylated hydroxytoluene; 18.0% by weight of mineral oil; and 27.2% by weight of hydrocarbon resin, based on the total weight of the drug-containing matrix layer.

The transdermal delivery system of the present invention may be prepared by forming said drug-containing matrix layer on a release layer, and then forming a backing layer thereon. For the release layer, conventional release liners or their laminates used in the technical field of a transdermal delivery system may be used. For example, there may be used a film, a paper, or a laminate thereof, which is made of polyethylene, polyester, polyvinyl chloride, polyvinylidene chloride, etc. coated with silicone resin or fluoride resin. And also, drug non-absorbable and flexible materials conventionally used in the field of a transdermal delivery system may be used as the backing layer (also referred to as "backing membrane"). For example, there may be used polyolefin, polyether, a multi-layer ethylene vinyl acetate film, polyester, polyurethane etc. For example, the transdermal delivery system of the present invention may be prepared by mixing donepezil or a pharmaceutically acceptable salt thereof, high molecular weight polyisobutylene, low molecular weight polyisobutylene, a stabilizer, an oil, and a thickening agent homogeneously with e.g., a roller mixer; casting the obtained mixture on e.g., a release liner coated with silicone, followed by drying; and then laminating a backing layer.

The present invention will be described in further detail with reference to the following examples and experimental examples. These examples and experimental examples are for illustrative purposes only and are not intended to limit the scope of the present invention.

Example 1

The transdermal delivery systems were prepared according to the components and amounts shown in Table 1. The amounts of Table 1 are % by weight based on the total weight of the drug-containing matrix layer of each transdermal delivery system. Specifically, donepezil free base, polyisobutylene having a weight-average molecular weight of 1,000,000 (Oppanol™ B 100, BASF, Germany) and polyisobutylene having a weight-average molecular weight of 75,000 (Oppanol™ B S15F, BASF, Germany), lauryl pyrrolidone (Surfadone™ LP-300, ISP, USA), butylated hydroxytoluene, mineral oil, and hydrocarbon resin (Kristalex™ F85, Hercules, USA) were mixed homogeneously using a roller mixer. Each resulting mixture was left for 1 hour to remove air bubbles, casted on a release liner coated with silicone, and then dried at 70° C. for 90 minutes. A polyethylene film was laminated on the resulting each layer to form a backing membrane, so as to prepare each donepezil-containing transdermal delivery system.

Each transdermal delivery system was applied onto hairless mouse skin to determine their skin permeation rates. Specifically, the skin was excised from hairless mouse (6 to 8 weeks old) right before the experiment. Each transdermal drug delivery system was attached on the isolated skin. Each resulting skin was fixed in each flow-through diffusion cell with a clamp thereof. To the receiver thereof, was added an isotonic phosphate buffer solution (pH 6.0). While the diffusion cell was maintained at 32.5° C. under stirring at 600 rpm with a magnetic stirrer, samples were collected at 0, 6, 12, 24, 36, 48, 60, and 72 hours. The samples were subject to quantitative analysis using high-performance liquid chromatography equipped with an ultraviolet spectrophotometer under the following conditions.

<Analysis Condition>

Column: Capcellpak C18, 4.6×150 mm, 5 μm

Mobile phase: Sodium decasulfonate (2.5 g) was dissolved completely in water (650 mL), followed by adding 70% perchloric acid solution (1 mL) and acetonitrile (350 mL) thereto. The obtained solution was filtered, sonicated for 10 minutes to remove bubbles, and then used as a mobile phase.

Temperature: 40° C.

Injection volume: 5 μl

Ultraviolet Spectrophotometer: 271 nm

Retention time: 18.5 min

And also, each transdermal delivery system was cut across with a knife to form a physical damage and then stored at the conditions of 25° C. and relative humidity of 60% for 6 months. Whether there is any crystal formation in each transdermal delivery system was observed with a microscope.

The cumulative permeation amounts (i.e., cumulative concentrations) measured in the above are shown in FIG. 1. The skin permeation rates (flux) calculated therefrom are shown in the following table 1. The results obtained by observing any crystal formation are also shown in the following table 1.

TABLE 1

| | | Example (% by weight) | | | |
|---|---|---|---|---|---|
| | Components | 1-1 | 1-2 | 1-3 | 1-4 |
| Active ingredient | Donepezil | 7.6 | 7.6 | 7.6 | 7.6 |
| Permeation enhancer | Lauryl pyrrolidone | 1.5 | 1.5 | 1.5 | 1.5 |
| Stabilizer | Butylated hydroxytoluene | 0.3 | 0.3 | 0.3 | 0.3 |
| High molecular weight polyisobutylene | Oppanol ™ B 100 | 22.7 | 30.3 | 15.1 | 34.0 |
| Low molecular weight polyisobutylene | Oppanol ™ B S15F | 22.7 | 15.1 | 30.3 | 11.3 |
| Oil | Mineral oil | 18.0 | 18.0 | 18.0 | 18.0 |
| Thickening agent | Kristalex ™ F85 | 27.2 | 27.2 | 27.2 | 27.2 |
| Skin permeation rate (μg/cm$^2$/hr) | | 7.2 | 4.5 | 5.2 | 5.0 |
| Crystal formation | | No | No | No | No |

From the results of Table 1, it can be seen that the transdermal delivery system prepared according to the present invention prevented the crystallization of donepezil effectively and maintained high skin permeation rate for a long period of time even though it contained the permeation enhancer in small amount (i.e., in about 1.5%). Among them, the transdermal delivery system in which the weight ratio of the high molecular weight polyisobutylene and the low molecular weight polyisobutylene was 1:1 showed the most excellent skin permeation rate.

Example 2

The transdermal delivery systems were prepared with the same procedures as in Example 1, except for using polyisobutylene having a weight-average molecular weight of 25,000 (Oppanol™ B 10, BASF, Germany) [Example 2-1] or polyisobutylene having a weight-average molecular weight of 200,000 (Oppanol™ B 30, BASF, Germany) [Example 2-2] instead of polyisobutylene having a weight-average molecular weight of 75,000. Each transdermal delivery system was applied onto human cadaver skin to determine their skin permeation rates. Specifically, each transdermal drug delivery system was attached on the human cadaver skin. Each resulting skin was fixed in each flow-through diffusion cell with a clamp thereof. To the receiver thereof, was added an isotonic phosphate buffer solution (pH 6.0). While the diffusion cell was maintained at 32.5° C. under stirring at 600 rpm with a magnetic stirrer, samples were collected at 0, 6, 12, 24, 48, 60, and 72 hours. The samples were subject to quantitative analysis using high-performance liquid chromatography equipped with an ultraviolet spectrophotometer under the same conditions as in Example 1. The cumulative permeation amounts (i.e., cumulative concentrations) measured in the above are shown in FIG. 2.

Figure 2:
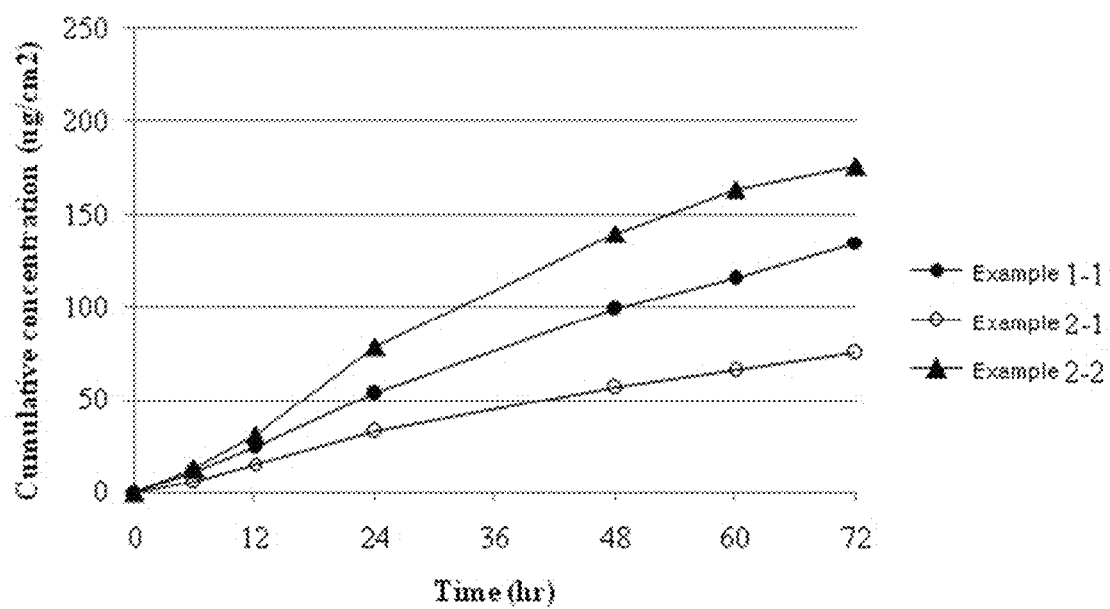
FIG. 2 shows the results obtained by measuring skin permeation rate changes (cumulative concentration) according to the weight-average molecular weights of the low molecular weight polyisobutylene.

As shown in the results of FIG. 2, the skin permeation rate increased with the increase of the molecular weight of the low molecular weight polyisobutylene, which is used together with the high molecular weight polyisobutylene. Therefore, it can be seen that the preferable molecular weight range of the low molecular weight polyisobutylene used together with the high molecular weight polyisobutylene is 25,000 to 200,000.

Example 3

The transdermal delivery systems were prepared with the same procedures as in Example 1, according to the components and amounts shown in Table 2. We evaluated the effects of amounts of the permeation enhancer on skin permeation rate of the transdermal delivery system. Skin permeation rate was determined according to the same procedures as in Example 2. The results thereof are shown in FIG. 3.

TABLE 2

|  | | Example [g (% by weight)] | | | |
| --- | --- | --- | --- | --- | --- |
|  | Components | 3-1 | 3-2 | 3-3 | 3-4 |
| Active ingredient | Donepezil | 0.50 | 0.50 | 0.50 | 0.50 |
| Permeation enhancer | Lauryl pyrrolidone | 0.00 (0% by weight) | 0.20 (2.3% by weight) | 0.50 (5.5% by weight) | 1.00 (10.5% by weight) |
| Stabilizer | Butylated hydroxytoluene | 0.03 | 0.03 | 0.03 | 0.03 |
| High molecular weight polyisobutylene | Oppanol™ B 100 | 2.00 | 2.00 | 2.00 | 2.00 |
| Low molecular weight polyisobutylene | Oppanol™ B S15F | 2.00 | 2.00 | 2.00 | 2.00 |
| Oil | Mineral oil | 1.60 | 1.60 | 1.60 | 1.60 |
| Thickening agent | Kristalex™ F85 | 2.40 | 2.40 | 2.40 | 2.40 |

Figure 3:
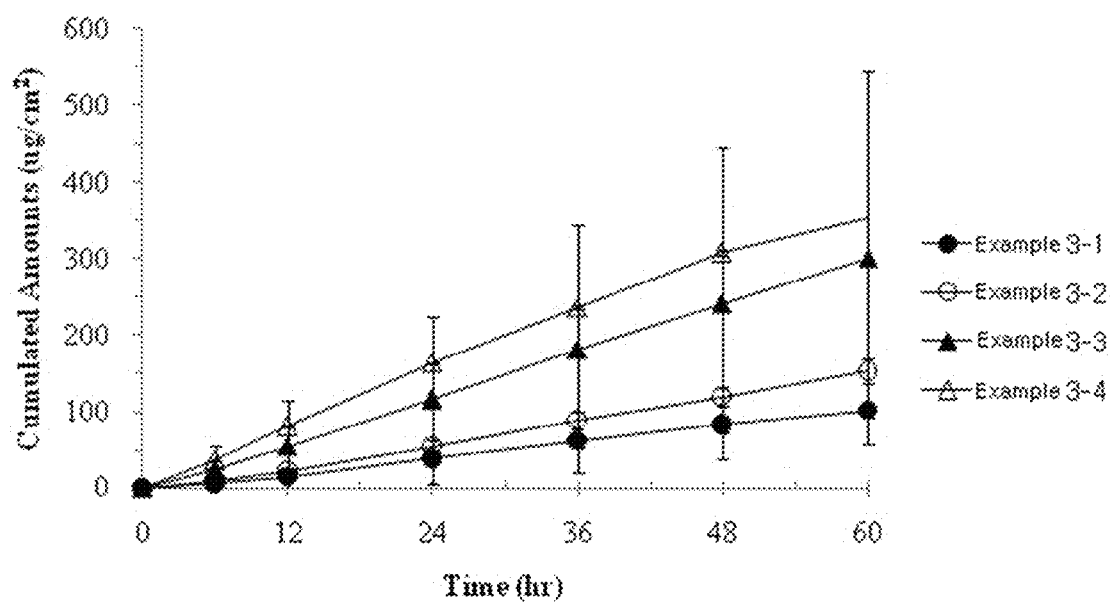
FIG. 3 shows the results obtained by measuring skin permeation rate changes (cumulative amount) according to amounts of the permeation enhancer.

From the results of FIG. 3, it can be seen that the cumulative concentration increased with the increase of the amount of the permeation enhancer.

Example 4

The transdermal delivery systems were prepared with the same procedures as in Example 1, according to the components and amounts shown in Table 3. We evaluated the effects of types of the stabilizer on stability of the transdermal delivery system. As a stabilizer, we used butylated hydroxytoluene (BHT) and butylated hydroxyanisole (BHA), having similar structure each other. The stability evaluation was performed under the accelerated condition (i.e., at 40° C. and relative humidity of 75%). The results thereof are shown in following Table 4.

TABLE 3

| | Example [g (% by weight)] | | | | | |
| --- | --- | --- | --- | --- | --- | --- |
| Components | 4-1 | 4-2 | 4-3 | 4-4 | 4-5 | 4-6 |
| Donepezil | 0.500 | 0.500 | 0.500 | 0.500 | 0.500 | 0.500 |
| Lauryl pyrrolidone | 0.150 | 0.150 | 0.150 | 0.150 | 0.150 | 0.150 |
| Butylated hydroxytoluene (BHT) | 0.015 (0.15% by weight) | 0.030 (0.30% by weight) | 0.100 (1.00% by weight) | — | — | — |
| Butylated hydroxyanisole (BHA) | — | — | — | 0.015 (0.15% by weight) | 0.030 (0.30% by weight) | 0.100 (1.00% by weight) |
| Oppanol™ B 100 | 2.00 | 2.00 | 2.00 | | | 2.00 |
| Oppanol™ B S15F | 2.00 | 2.00 | 2.00 | | | 2.00 |
| Mineral oil | 1.60 | 1.60 | 1.60 | | | 1.60 |
| Kristalex™ F85 | 2.40 | 2.40 | 2.40 | | | 2.40 |

TABLE 4

| Stability evaluation under the accelerated storage condition | | | | | |
| --- | --- | --- | --- | --- | --- |
| Time (M) | 0 M | 1.5 M | 3 M | 4.5 M | 6 M |
| Example 4-1 | 102.40 | 95.00 | 96.55 | 95.6 | 90.92 |
| Example 4-2 | 99.00 | 96.91 | 94.11 | 94.51 | 90.16 |
| Example 4-3 | 100.13 | 96.68 | 97.07 | 95.33 | 93.85 |
| Example 4-4 | 102.40 | 85.26 | — | — | — |
| Example 4-5 | 99.00 | 91.97 | — | — | — |
| Example 4-6 | 100.13 | 93.10 | — | — | — |

From the results of Table 4, it can be seen that, when butylated hydroxyanisole was used as a stabilizer, the amount of the active ingredient decreased by about 6.9 to 14.7% in 1.5 months. However, when butylated hydroxytoluene was used as a stabilizer, the amount of the active ingredient decreased only by about 3.3 to 5% in 1.5 months; and only by 6.1 to 9.8% in 6 months. And also, there is no significant difference in the amount of the active ingredient according to the amounts of butylated hydroxytoluene. Therefore, it can be seen that butylated hydroxytoluene is preferable as a stabilizer.

Experimental Example 1: Evaluation on Processability in Preparing a Drug-Containing Matrix Layer According to the Amounts of Donepezil Processability in preparing a drug-containing matrix layer according to the amounts of donepezil was evaluated, using the adhesive (i.e., the combination of polyisobutylene having a weight-average molecular weight 1,000,000 and polyisobutylene having a weight-average molecular weight 75,000). Amine-resistant silicone medical adhesive was used as a comparative adhesive. The processability evaluation in preparing a drug-containing matrix layer was carried out by observing whether there is any precipitation of the donepezil crystal in the respective adhesive with changing the amounts of donepezil. Table 5 shows the results obtained by mixing the respective adhesive with donepezil and then homogenizing for 24 hours without drying.

TABLE 5

| | Donepezil content | | | |
|---|---|---|---|---|
| | 2 W/W % | 5 W/W % | 7.6 W/W % | 10 W/W % |
| The combination of polyisobutylene having a weight-average molecular weight 1,000,000 and polyisobutylene having a weight-average molecular weight 75,000 | Clear solution | Clear solution | Clear solution | Clear solution |
| Amine-resistant silicone adhesive | Clear solution | Precipitated | Precipitated | Precipitated |

Figure 4A:
FIG. 4a shows the results (appearance) obtained by adding donepezil in a concentration of 7.6% by weight to a combination of polyisobutylene having a weight-average molecular weight 1,000,000 and polyisobutylene having a weight-average molecular weight 75,000.
Figure 4B:
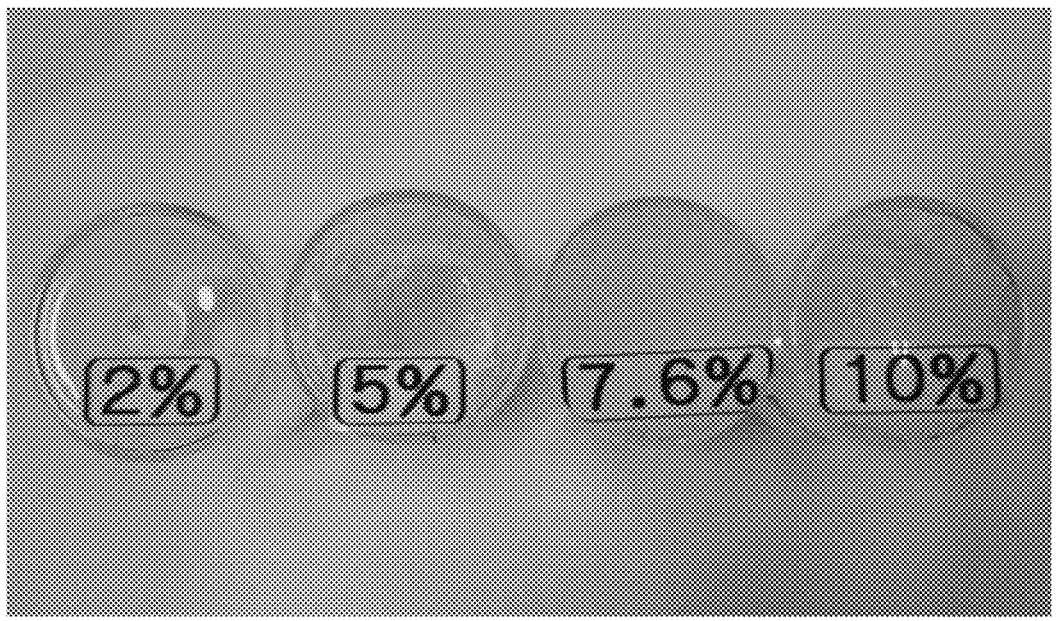
FIG. 4b shows the results (appearance) obtained by adding donepezil in concentrations of 2, 5, 7.6, and 10% by weight respectively to amine-resistant silicone adhesive.

And also, FIG. 4a shows the result (appearance) obtained by adding donepezil in the concentration of 7.6% by weight to the combination of polyisobutylene having a weight-average molecular weight 1,000,000 and polyisobutylene having a weight-average molecular weight 75,000; and FIG. 4b shows the results (appearance) obtained by adding donepezil in the concentrations of 2, 5, 7.6, and 10% by weight to the amine-resistant silicone adhesive.

As shown in Table 5 and FIG. 4, when the specific combination of adhesives according to the present invention was used, the resulting mixture showed a clear solution at donepezil content of 7.6% by weight. However, when the silicone type adhesive was used, the resulting mixture showed a clear solution only at donepezil content of 2% by weight. That is, when the silicone type adhesive was used, solid crystal in the mixture was observed at donepezil content of not less than 5% by weight. These results mean that, when the silicone type adhesive was used, a drug-containing matrix layer cannot be formed at high amounts of donepezil.

Figure 5A:
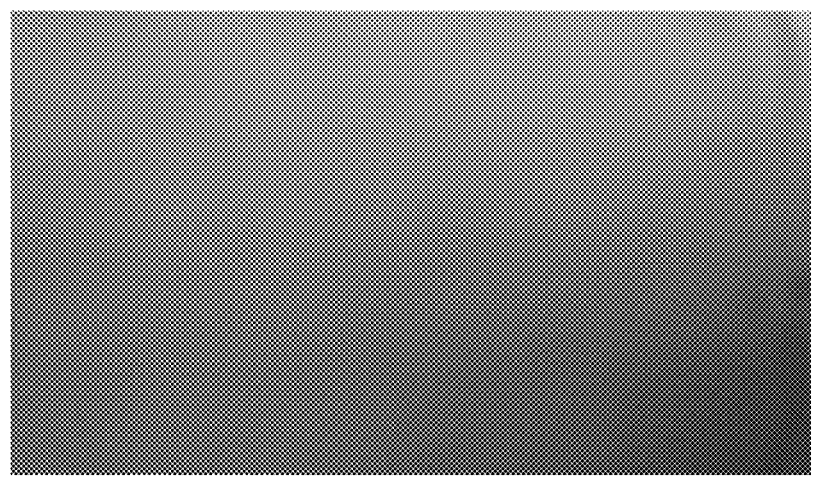
FIGS. 5a and 5b show the appearance of the drug-containing matrix layer prepared according to the present invention and the appearance of the same after applying it to human skin, respectively.
Figure 5B:
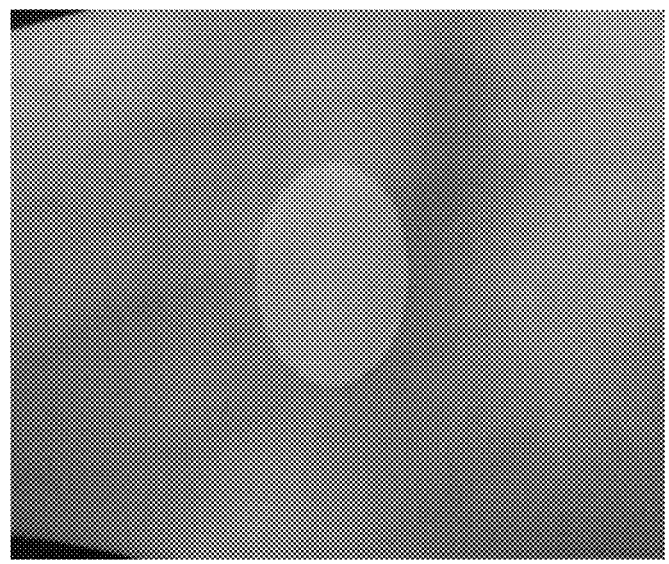

Experimental Example 2: Evaluation on the Appearance of the Drug-Containing Matrix Layer Before and after Applying to Human Skin FIGS. 5a and 5b show the appearance of the drug-containing matrix layer prepared in Example 1-1 and the appearance of the same after applying to human skin, respectively. And also, FIGS. 6a and 6b show the appearance of the comparative drug-containing matrix layer (prepared according to the same procedures as in Example 1-1, expect for using donepezil in the concentration of 2% by weight and the amine-resistant silicone adhesive as an adhesive) and the appearance of the same after applying to human skin, respectively.

Figure 6A:
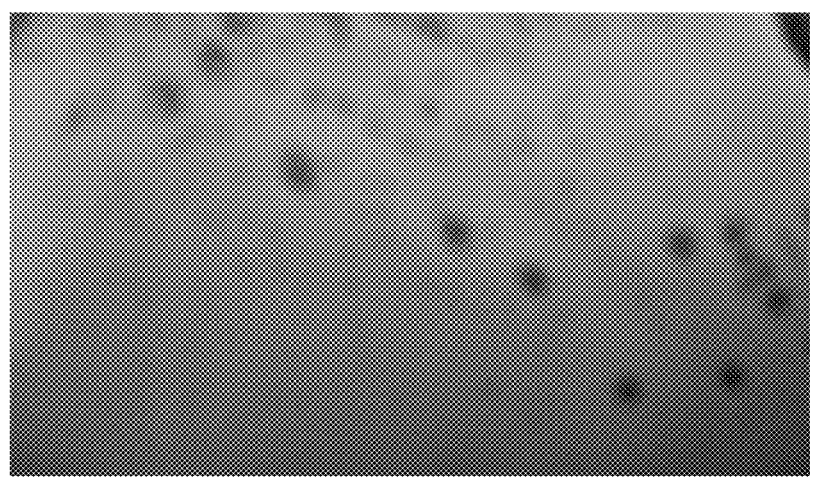
FIGS. 6a and 6b show the appearance of the drug-containing matrix layer obtained by adding donepezil in a concentration of 2% by weight to amine-resistant silicone adhesive and the appearance of the same after applying it to human skin.
Figure 6B:

As shown in FIGS. 5a and 6a, the drug-containing matrix layer prepared according to the present invention showed homogeneous state without bubbles in the matrix layer, while the comparative drug-containing matrix layer showed bubbles having various sizes. And also, as shown in FIGS. 5b and 6b, the initial shape of the drug-containing matrix layer prepared according to the present invention was maintained during the attachment without any deformation (i.e., without the adhesive in the matrix layer being shoved out after the attachment on the skin). However, when the comparative drug-containing matrix layer was applied, the adhesive in the matrix layer was shoved out after the attachment on the skin (i.e., deformation was observed).

Experimental Example 3: Stability Test

Figure 7A:
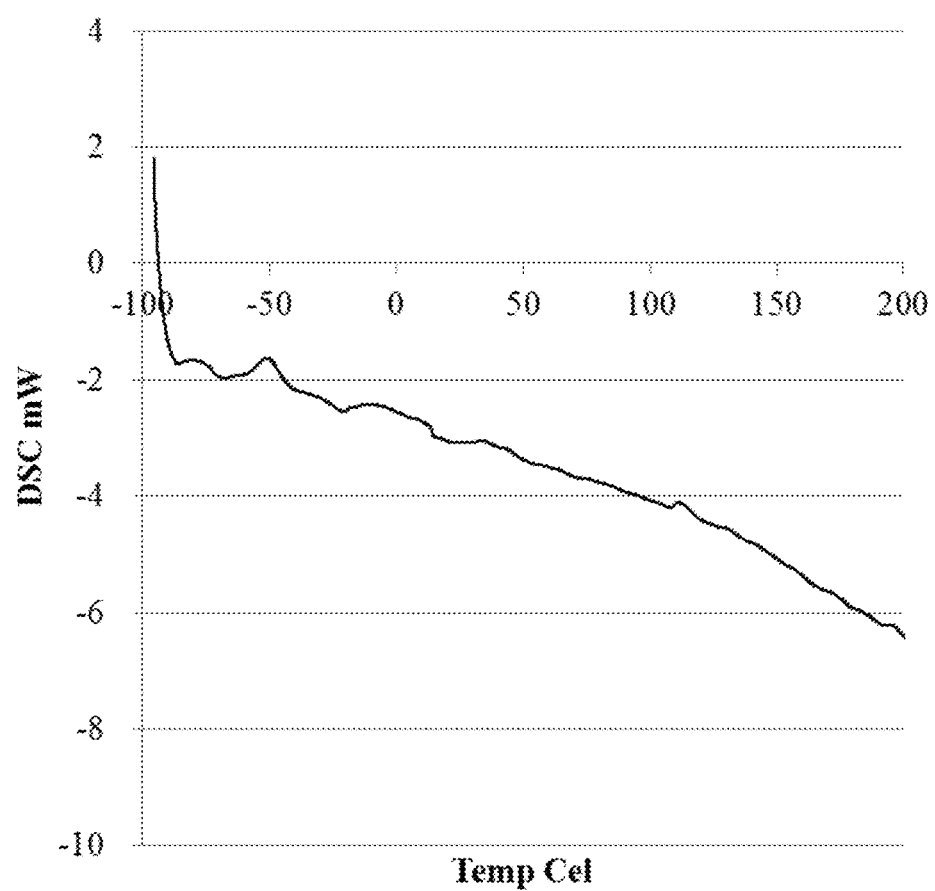

In order to determine any polymer denaturation or any change in physicochemical properties in the transdermal delivery system, Differential scanning calorimetry analysis was performed using a Differential Scanning calorimeter (DSC) after storing the transdermal delivery system prepared in Example 1-1 at the room temperature condition (25° C., relative humidity of 60%) or at the accelerated condition (40° C., relative humidity of 75%), for 1 month. The results thereof are shown in FIGS. 7a and 7b. FIG. 7a shows the result of the differential scanning calorimetry analysis obtained after storing the transdermal delivery system prepared in Example 1-1 at the room temperature condition for 1 month. FIG. 7b shows the result of the differential scanning calorimetry analysis obtained after storing the transdermal delivery system prepared in Example 1-1 at the accelerated storage condition for 1 month. As shown in FIGS. 7a and 7b, the transdermal delivery system according to the present invention did not show significant difference, when storing at the room temperature condition and at the accelerated storage condition for 1 month.

Experimental Example 4: Evaluation on Skin Irritation

Skin irritation was evaluated after applying the transdermal delivery systems obtained in Example 3-1 to 3-4 to healthy volunteers' skin for 7 days. As degrees of skin irritation (i.e., 0 to 5), 0 was assigned to 'no skin irritation' and 5 was assigned to 'maximum skin irritation'. The results thereof are shown in Table 6.

TABLE 6

| Time (day) | 0 day | 1 day | 2 day | 4 day | 7 day |
|---|---|---|---|---|---|
| Example 3-1 | 0 | 0 | 0 | 0 | 0 |
| Example 3-2 | 0 | 0 | 0 | 1 | 1 |
| Example 3-3 | 0 | 1 | 1 | 2 | 4 |
| Example 3-4 | 0 | 1 | 2 | 3 | 5 |

From the results of Table 6, it can be seen that skin irritation increased significantly when the permeation enhancer was used in the amounts above 3% by weight (Examples 3-3 and 3-4) based on the total weight of the drug-containing matrix layer. However, almost no skin irritation was shown when the permeation enhancer was used in the amount of not more than 3% by weight (Examples 3-1 and 3-2) based on the total weight of the drug-containing matrix layer.

Experimental Example 5: Pharmacokinetic Evaluation

Pharmacokinetic evaluation was performed on the transdermal delivery system prepared according to the present invention and the comparative formulation (i.e., donepezil-containing oral tablet). Specifically, the transdermal delivery system prepared in Example 1-1 was used for the test group and the donepezil-containing oral tablet (Aricept 5 mg, Eisai) for the control group. The transdermal delivery system prepared in Example 1-1 was applied to healthy volunteers' skin of the test group (n=7) and Aricept 5 mg tablet was orally administered to another healthy volunteers of the control group (n=7).

Figure 8:
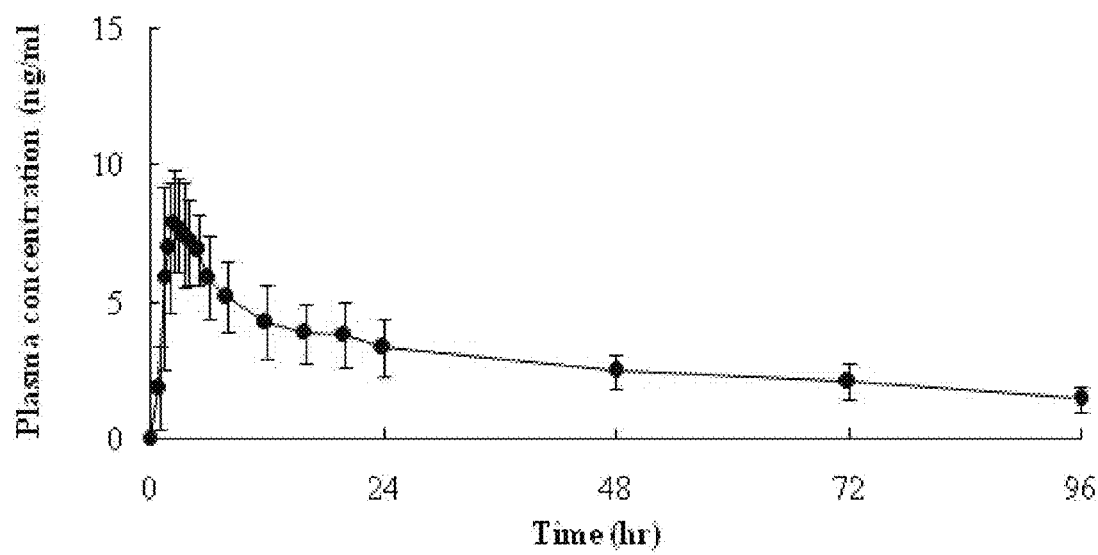
FIG. 8 shows blood concentration profile obtained from single oral administration of donepezil 5 mg tablet (Aricept 5 mg) to healthy volunteers.

To compare the pharmacokinetic profile of the transdermal delivery system according to the present invention with that of the donepezil-containing oral tablet, we used a simulated pharmacokinetic profile of multiple-administrations for 7 day, which was obtained by simulating with the pharmacokinetic parameters obtained from the single oral administration. The simulated pharmacokinetic profile, instead of performing multiple daily administrations for 7 days, was used to avoid the difficulties in the clinical study involving the repeated oral administrations for 7 days. After single oral administration of the donepezil 5 mg tablet (Aricept 5 mg) to healthy volunteers, blood samples were collected at a pre-determined interval and then analyzed to measure the donepezil concentrations thereof. FIG. 8 shows the blood concentration profile obtained from the analysis. And also, Table 7 shows the pharmacokinetic parameters obtained from the results of FIG. 8.

TABLE 7

| Pharmacokinetic parameter | Value |
| --- | --- |
| Tmax | 2.5 hr |
| Cmax (Maximum plasma concentration) | 7.9 ng/mL |
| $t_{1/2}$ | 57.9 hr |
| AUC (Area Under the Curve) | 399.2 ng*hr/mL |
| Volume of distribution | 1045533.1 mL |
| Clearance | 12526.2 mL/hr |

Figure 9:
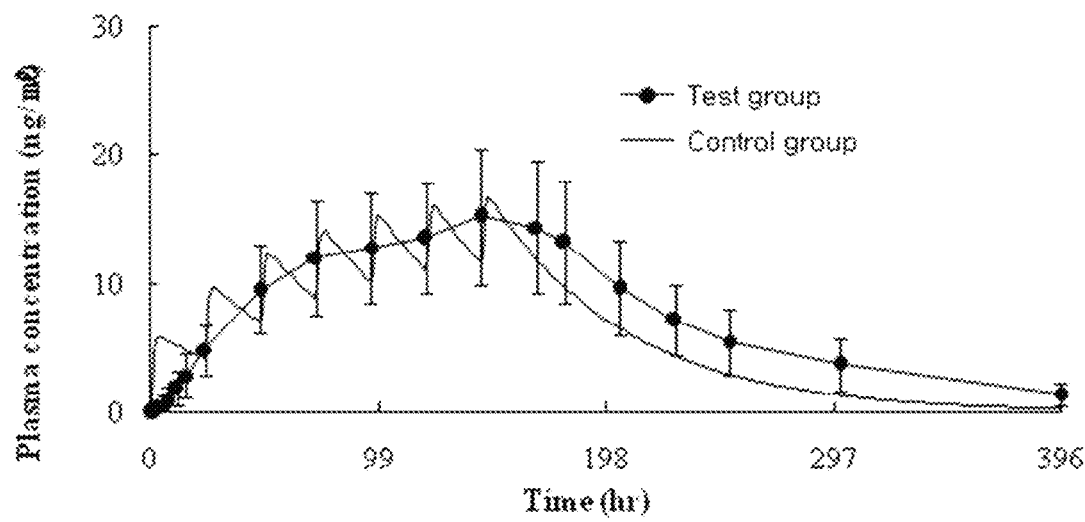
FIG. 9 shows the comparison of blood concentration profile of the transdermal delivery system according to the present invention and a simulated blood concentration profile of once-daily multiple-oral administrations of Donepezil 5 mg tablet for 7 days.

The pharmacokinetic profile of once-daily multiple oral administrations for 7 days was obtained by simulating with the pharmacokinetic parameters obtained from the above single oral administration using a Simulation Software (Pharsight's Phoenix WinNonlin) Table 8 and FIG. 9 show the pharmacokinetic parameters obtained from applying the transdermal delivery system prepared according to the present invention (the transdermal delivery system of Example 1-1); and the pharmacokinetic parameters obtained from the simulated pharmacokinetic profile of once-daily multiple oral administrations for 7 days.

TABLE 8

| | Cmax (ng/mL) | | AUC (ng*hr/mL) | |
| --- | --- | --- | --- | --- |
| Group | Aricept 5 mg (7 days, simulated) | Transdermal delivery system of Example 1-1 (measured) | Aricept 5 mg (7 days, simulated) | Transdermal delivery system of Example 1-1 (measured) |
| 1 | 25.1 | 13.6 | 3957.6 | 2621.7 |
| 2 | 15.6 | 15.5 | 2097.5 | 3167.5 |
| 3 | 21.9 | 14.7 | 3267.9 | 3300.3 |
| 4 | 17.8 | 15.5 | 3264.5 | 2694.5 |
| 5 | 14.6 | 8.7 | 2308.1 | 1821.6 |
| 6 | 11.2 | 25.9 | 1597.5 | 5351.7 |
| 7 | 20.2 | 12.6 | 3168.7 | 2392.2 |
| Mean | 18.1 | 15.2 | 2808.8 | 3049.9 |

From the results of Table 8 and FIG. 9, it can be seen that the pharmacokinetic parameters of the two formulations were very similar each other; and that the pharmacokinetic profile of the transdermal delivery system obtained according to the present invention was also very similar to that of multiple-oral administrations for 7 days.

The invention claimed is:
1. A transdermal delivery system consisting of a backing layer, a drug-containing matrix layer, and a release layer, wherein the drug-containing matrix layer consists of 7.6% by weight of donepezil or a pharmaceutically acceptable salt thereof; 22.7% by weight of polyisobutylene having a weight-average molecular weight of 1,000,000; 22.7% by weight of polyisobutylene having a weight-average molecular weight of 75,000; 1.5% by weight of lauryl pyrrolidone; 0.3% by weight of butylated hydroxytoluene; 18.0% by weight of mineral oil; and 27.2% by weight of hydrocarbon resin, based on the total weight of the drug-containing matrix layer.

* * * * *